United States Patent
McIvor et al.

(10) Patent No.: US 6,485,722 B1
(45) Date of Patent: Nov. 26, 2002

(54) METHOD FOR SELECTIVE ENGRAFTMENT OF DRUG-RESISTANT HEMATOPOIETIC STEM CELLS

(75) Inventors: R. Scott McIvor, St. Louis Park, MN (US); Rohaizah I. James, Fridley, MN (US); Chad May, New York, NY (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/142,126

(22) PCT Filed: Feb. 26, 1997

(86) PCT No.: PCT/US97/02772

§ 371 (c)(1),
(2), (4) Date: Jul. 6, 1999

(87) PCT Pub. No.: WO97/32025

PCT Pub. Date: Sep. 4, 1997

Related U.S. Application Data (60) Provisional application No. 60/012,677, filed on Mar. 1, 1996.

(51) Int. Cl.$^7$ .......................... A61K 31/70; A01N 63/00; C12N 5/00

(52) U.S. Cl. .................. 424/93.21; 424/93.1; 424/93.2; 435/325; 514/44

(58) Field of Search .................. 424/93.1; 435/240, 435/455, 440, 325; 514/44; 800/21, 8; 536/23.1

(56) References Cited

U.S. PATENT DOCUMENTS

| | | | | |
|---|---|---|---|---|
| 5,436,151 A | | 7/1995 | McGlave et al. | 435/240.1 |
| 5,460,964 A | * | 10/1995 | McGlave | 435/240.01 |

FOREIGN PATENT DOCUMENTS

| | | | |
|---|---|---|---|
| EP | 0 341 966 | 11/1989 | C12Q/1/24 |

OTHER PUBLICATIONS

Li et al., Blood 83(11):3403–3408, Jun. 1994.*
Flasshove et al., Leukemia 9:534–537, Oct. 1995.*
May et al., Blood 86(6):2439–2448, Oct. 1995.*
Sorrentino et al., Science 257:99–103, Jul. 1992.*
Morris et al., Biochemical Pharmacology 47(7):1207–1220, Oct. 1994.*
Corey et al., Blood 75(2):337–343, Jan. 1990.*
Bodine et al., Blood 82(7):1975–1980, Oct. 1993.*
Banerjee, D., et al., "Gene therapy utilizing drug resistance genes: a review", *Stem Cells*, 12, 378–385, (1994).
Boesen, J., et al., "Circumvention of chemotherapy–induced myelosuppression by transfer of the mdr1 gene", *Biotherapy*, 6, 291–302, (1994).
Bordignon, C., et al., "Transfer of the ADA Gene into Bone Marrow Cells and Peripheral Blood Lymphocytes for the Treatment of Patients Affected by ADA–deficient SCID", *Hum, Gene Ther.*, 4(4), 513–520, (1993).
Brenner, M.K., et al., "Gene transfer into human hemopoietic progenitor cells", *British Medical Bulletin*, 51(1), 167–191, (1995).
Flasshove, M., et al., "Ex vivo expansion and selection of human CD34+ peripheral blood progenitor cells after introduction of a mutated dihydrofolate reductase cDNA via a retroviral vector", *Blood*, 85 (2), pp. 566–574, (Jan. 15, 1995).
Gartner, S., et al., "Long–term culture of human bone marrow cells", *Proc Natl Acad Sci USA*, 77(8), 4756–4759, (1980).
Gordon, M.Y., et al., "Characterisation of stroma–dependent blast colony–forming cells in human marrow", *J Cell Physiol*, 130(1), 150–156, (1987).
Hock, R.A., et al., "Retrovirus–mediated transfer and expression of drug resistance genes in human haematopoietic progenitor cells", *Nature*, 320, 275–277, (1986).
Kwok, W.W., et al., "Retroviral transfer of genes into canine hemopoietic progenitor cells in culture: a model for human gene therapy", *Proc Natl Acad Sci USA*, 83(12), 4552–4555, (1986).
Moore, M.A., "Ex Vivo Expansion and Gene Therapy Using Cord Blood CD34+ Cells", *Journal of Hematotherapy*, 2 (2), pp. 221–224, (1993).
Podda, S., et al., "Transfer and expression of the human multiple drug resistance gene into live mice", *Proc Natl Acad Sci USA*, 89(20), 9676–9680, (1992).
Reimann, J., et al., "Selective Engraftment of Memory CD4+ T Cells with an Unusual Recircualtion Pattern and a Diverse T Cell Receptor–V beta Repertoire into SCID Mice", *Eur. J. Immunol.*, 23(2), 350–356, (1993).
Slovick, F.T., et al., "Survival of granulocytic progenitors in the nonadherent and adherent compartments of human long–term marrow cultures", *Exp Hematol*, 12(5), 327–338, (1984).
Spangrude, G.J., et al., "Purification and characterization of mouse hematopoietic stem cells", *Science*, 241, 58–62, (1988).
Stead, R.B., et al., "Canine model for gene therapy: Inefficient gene expression in dogs reconstituted with autologous marrow infected with retroviral vectors", *Blood*, 71(3), 742–747, (1988).
Vinh, D.B., et al., "Selective expression of methotrexate–resistant dihydrofolate reductase (DHFR) activity in mice transduced with DHFR retrovirus and administered methotrexate", *J Pharmacol Exp Ther*, 267(2), 989–996, (1993).
Williams, D.A., et al., "Protection of bone marrow transplant recipients from lethal doses of methotrexate by the generation of methotrexate–resistant bone marrow", *J Exp Med*, 166(1), 210–218, (1987).
Zhao, S., et al., "Long–term protection of recipient mice from lethal doses of methotrexate by marrow infected with a double–copy vector retrovirus containing a mutant dihydrofolate reductase", *Cancer Gene Therapy*, 1(1), 27–33, (1994).

* cited by examiner

*Primary Examiner*—Deborah Crouch
*Assistant Examiner*—Joseph Woitach
(74) *Attorney, Agent, or Firm*—Schwegman, Lundberg, Woessner & Kluth, P.A.

(57) ABSTRACT

A method to increase the efficiency of hematopoietic stem cell engraftment in vivo is provided.

34 Claims, 2 Drawing Sheets

METHOD FOR SELECTIVE ENGRAFTMENT OF DRUG-RESISTANT HEMATOPOIETIC STEM CELLS

CROSS-REFERENCE TO RELATED APPLICATIONS

This application is a national stage filing of PCT/US97/02772, filed Feb. 26, 1997, which claims the benefit of the filing date of U.S. application Ser. No. 60/012,677, filed Mar. 1, 1996.

BACKGROUND OF THE INVENTION

As many hereditary diseases are a result of defects in single genes, there are many potential applications of gene therapy in the treatment of single gene disorders. Moreover, gene therapy can also be useful in the treatment of acquired diseases, e.g., cancer and infectious diseases. In particular, many of these diseases can potentially be treated or prevented by the introduction of a therapeutic gene(s) into hematopoietic stem cells (HSC), since the entire hematopoietic system can theoretically be regenerated from a single stem cell.

With a few exceptions (e.g., hormones), most anticancer drugs used in the clinic today cause moderate to severe bone marrow toxicity (e.g., vinblastine, cisplatin, methotrexate, alkylating agents, and anthracyclines). The introduction of a gene that confers resistance to a chemotherapeutic drug (termed a drug resistance gene) into HSC can convert these bone marrow progenitor cells to a drug resistant state, thus allowing larger than conventional doses of chemotherapeutic agents to be administered safely to patients, without toxicity to bone marrow, the gastrointestinal tract, and other normal proliferating tissue.

The first eukaryotic drug resistance gene to be transferred to reconstituting bone marrow cells was a methotrexate (MTX) resistant rodent dihydrofolate reductase (mDHFR) gene. Mice transplanted with cells transduced with a mDHFR containing retroviral vector were protected from methotrexate induced myelosuppression (Corey et al., *Blood*, 75, 337 (1990); Williams et al., *J. Exp. Med.* 166, 210 (1987)). Subsequent experiments have suggested that methotrexate can also be used to select for murine hemopoietic cells expressing transferred MDHFR genes (Vinh and McIvor, *J. Pharmacol. Exp. Ther.*, 267, 989 (1993)).

Transfer of the human mdr1 gene to hemopoietic cells has also been described. P-glycoprotein, the product of the mdr1 gene, functions as a drug efflux pump and confers resistance to a wide variety of naturally occurring chemotherapeutic agents. Mice transplanted with mdr1 transduced cells showed attenuation of taxol induced myelosuppression (Sorrentino et al., *Science*, 257, 99 (1992); Hanania et al., *Blood*, 82, 1260 (1990)). In taxol treated animals, the proportion of circulating leukocytes transduced with the mdr1 virus increased with drug treatment, suggesting that cells expressing the transferred mdr1 gene can be dominantly selected in vivo with taxol (Sorrentino et al., supra; Podda et al., *Proc. Nat'l Acad. Sci. USA*, 89, 9676 (1992)). More recent work has suggested that the mdr1 gene can be used to select for the presence of other therapeutic genes when the therapeutic genes are linked to the mdr1 cDNA in bicistronic retroviral vectors. Thus, drug resistance genes can be used to attenuate drug induced myelosuppression and can act as dominant selectable markers for genetically altered hemopoietic cells.

While HSC are tempting targets for gene transfer, these cells can be transduced with only limited efficiency, since generally less than 0.01% of the cells in bone marrow are HSC. This limits the implementation of clinical protocols based on gene modified HSC. Moreover, even if a therapeutic gene can be stably integrated into HSC, once transferred to a recipient, the transgenic HSC have no selective growth advantage relative to their nontransgenic counterparts. Without such an advantage, the engraftment of HSC containing the therapeutic gene is uncertain and, thus, the curative effect of the expression of the therapeutic gene in HSC and their progeny is unlikely.

One way to increase the representation of successfully transduced HSC would be to mediate selective engraftment by expression of a drug resistance gene. Although selective expansion of hematopoietic cells derived from transduced stem cells has been demonstrated for stem cells transduced with drug resistance genes, the ability of these drug-resistance genes to confer selective engraftment of HSC has not been established by long-term reconstitution studies.

Thus, what is needed is an improved method to select for engraftment of transplanted hematopoietic cells.

SUMMARY OF THE INVENTION

The present invention provides a method for selective engrafinent of hematopoietic stem cell in vivo. The method comprises administering to a mammal a population of stem cells comprising transgenic stem cells, the genome of which has been augmented by a first preselected DNA segment which is operably linked to a promoter functional in stem cells. The first preselected DNA segment encodes resistance to an agent which is normally toxic to stem cells. A preferred embodiment of the invention includes a first preselected DNA segment which encodes resistance to a chemotherapeutic agent, such as an antineoplastic or cytotoxic agent. The genome of the transgenic stem cells can also be augmented by a second preselected DNA segment which encodes a therapeutic agent. The expression of the first preselected DNA segment in the transgenic stem cells is effective to impart resistance or tolerance to said transgenic cells to an amount of the agent which is toxic to the corresponding nontransgenic stem cells. The agent is administered to said mammal in an amount, and for a time, so as to increase the engraftment and proliferation of transgenic stem cells relative to the engraftment and proliferation of nontransgenic stem cells. A preferred embodiment of the invention includes daily administration of the agent.

As used herein, the term "hematopoietic stem cells (HSC)" means a population of primitive progenitor cells which can provide long term reconstitution of both myeloid and lymphoid cell lineages in a host.

As used herein, a cell which is "resistant or tolerant" to an agent means a cell which has been genetically modified so that the cell proliferates in the presence of an amount of an agent that inhibits or prevents proliferation of a cell without the modification.

As used herein, a preselected DNA segment that encodes "resistance" to an agent, such as a preselected DNA segment that encodes resistance to a chemotherapeutic agent, e.g. methotrexate, means that the expression of the preselected DNA segment in a cell permits that cell to proliferate in the presence of the agent to a greater extent than the proliferation of a corresponding cell without the preselected DNA segment. A preselected DNA segment of the invention can encode resistance to methotrexate, vinblastine, cisplatin, alkylating agents, or anthracyclines, their analogs or derivatives, and the like.

As used herein with respect to an agent, the term "therapeutically effective amount" means an amount of the agent that inhibits or prevents proliferation of untransformed cells in a mammalian host.

As used herein, the term "a preselected DNA segment encoding a therapeutic agent" is defined as a preselected DNA segment encoding any polypeptide, peptide, protein, or sense or antisense RNA that imparts a desired effect to the mammal when it is produced by the cells of said mammal, including, but not limited to, an enzyme (e.g, adenosine deaminase, thymidine kinase, glucose cerebrosidase), a hormone (e.g., human growth hormone, insulin), a cytokine, clotting factors, a hormonal regulator (e.g., amylin, erythropoietin), antisense oligonucleotides (e.g., antisense to the mRNA encoding $P210^{BCR/ABL}$) and the like.

As used herein, the term "engraftment" with respect to HSC means that HSC which are introduced into a recipient are localized in the bone marrow of the recipient and can provide long term reconstitution of both myeloid and lymphoid cell lineages in that recipient.

DETAILED DESCRIPTION OF THE INVENTION

To improve cancer therapy and selective engrafiment of transfused or transplanted tissues, drug resistance genes can be transferred into cells, e.g., HSC, which are normally drug sensitive. The transfer of the drug resistance gene into HSC protects the transplanted transgenic HSC from the toxic side effects of chemotherapy with an antineoplastic or cytotoxic agent. The present method thus allows the administration of higher doses of the chemotherapeutic agent to the host. The transfer of drug resistance genes into HSC also permits the transgenic HSC and their progeny to be selectively enriched in vivo, as HSC and their progeny which contain and express the drug resistance gene and other genes which are co-introduced into those cells, will survive and multiply relative to cells which lack the drug resistance gene in the presence of the drug. Although selective expansion of transduced stem cells into more differentiated blood cell types has been previously demonstrated, the selective engraftment of primitive stem cells based on expression of a drug resistance gene has not.

In a preferred embodiment of the invention, the genome of HSC is transformed with a preselected DNA segment which encodes resistance to a chemotherapeutic agent, such as methotrexate, to yield transgenic HSC. A population of HSC which includes the transgenic HSC is then introduced into a recipient mammal. The administration of the chemotherapeutic agent to the recipient inhibits or greatly reduces the proliferation of untransformed HSC which are undergoing engraftment, while the transgenic HSC which are undergoing engraftment survive and proliferate, i.e., they are resistant to the agent. The proliferation of the engrafted transgenic HSC results in an increase in the relative number of engrafted transgenic HSC, as well as an increase in the number of differentiated progeny which are derived from the engrafted transgenic HSC. These progeny contain the preselected DNA segment and thus are resistant to the chemotherapeutic agent. Transplanted HSC do not significantly contribute to differentiated progeny lineages for at least about 2–4 weeks after the stem cells have been transplanted.

A. Hematopoietic Stem Cells

The human hematopoietic system is populated by a hierarchy of cells with differing capacities for self renewal, proliferation and differentiation. There are cells of several different lineages. These "blood cells" may appear in bone marrow, the thymus, lymphatic tissue(s) and in peripheral blood. Within any specific lineage, there are a number of maturational stages. In most instances, the more immature developmental stages occur within bone marrow while the more mature and final stages of development occur in peripheral blood.

There are two major lineages: The myeloid lineage which matures into red blood cells, granulocytes, monocytes and megakaryocytes; and the lymphoid lineage which matures into B lymphocytes and T lymphocytes. Within each lineage and between each lineage, antigens are expressed differentially on the surface and in the cytoplasm of the cells in a given lineage. The expression of one or more antigens and/or the intensity of expression can be used to distinguish between maturational stages within a lineage and between lineages.

Assignment of a cell to a lineage and to a maturational stage within a cell lineage indicates lineage commitment. There are cells, however, which are uncommitted to any lineage (i.e., "progenitor" cells) and which, therefore, retain the ability to maintain their population and to differentiate into each lineage. These undifferentiated, pluripotent progenitor cells are referred to as the "hematopoietic stem cells (HSC)."

All of mammalian hematopoietic cells can, in theory, be derived from a single stem cell. In vivo, the stem cell is able to self-renew, so as to maintain a continuous source of pluripotent cells. In addition, when subject to particular environments and/or factors, the stem cells may differentiate to yield dedicated progenitor cells, which in turn may serve as the ancestor cells to a limited number of blood cell types. These ancestor cells will go through a number of stages before ultimately yielding mature cells.

The benefit of identifying and obtaining a pure population of stem cells is most readily recognized in the field of gene therapy. Gene therapy seeks to replace or repopulate the cells of the hematopoietic system which contain a defective gene with cells that do not contain the defective gene but instead contain a "normal" gene. Thus, using conventional recombinant DNA techniques, a "normal" gene is isolated, placed into a viral or other vector, and the vector is transfected into a cell capable of expressing the product coded for by the gene. The cell then must be introduced into the patient. If the "normal" gene product is produced in sufficient quantity, the patient is "cured" of the condition.

However, the transformed cells must be capable of continual regeneration as well as growth and differentiation. Thus, while Kwok et al. (*PNAS USA*, 83, 4552 (1986)) demonstrated that gene therapy was possible using retroviral vector-transduced progenitor cells in dogs, the transduced cells were not capable of self-renewal. Thus, the "cure" was only temporary.

Other difficulties encountered in stem cell gene therapy are due to the fact that the stem cell population constitutes only a small percentage of the total number of leukocytes in bone marrow. Weissman et al. (EPO 341,966) reported that murine bone marrow contains only about 0.02–0.1% pluripotent stem cells. Moreover, the introduction of between 20–30 of these stem cells per recipient are necessary to rescue 50% of a group of lethally-irradiated mice. See Weissman et al., supra and Spangrude et al., *Science*, 241, 58 (1988).

The development of cell culture media and conditions to maintain stem cells in vitro for the extended periods of time required for the procedures involved in gene therapy, identification of growth factors, thorough characterization of cell morphologies and the like, has presented a unique set of obstacles. To date, successful in vitro stem cell cultures have depended on the ability of the laboratory worker to mimic the conditions which are believed to be responsible for maintaining stem cells in vivo.

For example, hematopoiesis occurs within highly dense cellular niches within the bone marrow in the adult and in similar niches within the fetal yolk sac and liver. Within these niches, stem cell differentiation is regulated, in part, through interactions with local mesenchymal cells or stromal cells. Mammalian hematopoiesis has been studied in vitro through the use of various long-term marrow culture systems. T. M. Dexter et al., in *J. Cell Physiol.*, 91, 335 (1977) described a murine system from which spleen colony-forming units (CFU-S) and granulocyte/macrophage colony forming units (CFU-GM) could be detected for several months, with erythroid and megakaryocytic precursors appearing for a more limited time. Maintenance of these cultures was dependent on the formation of an adherent stromal cell layer composed of endothelial cells, adipocytes, reticular cells, and macrophages.

These methods were soon adapted for the study of human bone marrow. Human long-term culture system were reported to generate assayable hematopoietic progenitor cells for 8 or 9 weeks, and, later, for up to 20 weeks (See, S. Gartner, et al., *PNAS USA*, 77, 4756 (1980); F. T. Slovick et al., *Exp. Hematol.*, 12, 327 (1984)). Such cultures were also reliant on the preestablishment of a stromal cell layer which must frequently be reinoculated with large, heterogeneous populations of marrow cells. Hematopoietic stem cells have been shown to home and adhere to this adherent cell multilayer before generating and releasing more committed progenitor cells (M. Y. Gordon et al., *J. Cell Physiol.*, 130, 150 (1987)).

Stromal cells are believed to provide not only a physical matrix on which stem cells reside, but also to produce membrane-contact signals and/or hematopoietic growth factors necessary for stem cell proliferation and differentiation. This heterogenous mixture of cells comprising the adherent cell layer presents an inherently complex system from which the isolation of discrete variables affecting stem cell growth has proven difficult. Furthermore, growth of stem cells on a stromal layer makes it difficult to recover the hematopoietic cells or their progeny efficiently.

Recently, methods have been developed to culture stem cells effectively in vitro, in stromal feeder cell-conditioned medium, with or without added cytokines, as taught in U.S. Pat. Nos. 5,436,151 and 5,460,964.

B. Mammalian Gene Transfer

Gene transfer methods used to transform mammalian cells can be classified as physical or biological processes. Physical methods include DNA transfection, lipofection, particle bombardment, microinjection and electroporation. Biological methods include the use of DNA and RNA viral vectors. The main advantage of physical methods is that they are not associated with the pathological or oncogenic processes of viruses. However, they are less precise, often resulting in multiple copy insertions, random integration, disruption of foreign and endogenous gene sequences, and unpredictable expression. For human gene therapy, it is desirable to use an efficient means of precisely inserting a single copy of a preselected gene into the host genome. Viral vectors, and especially retroviral and adenovirus associated viral vectors, have become the most widely used method for inserting genes into human cells. Other viral vectors are derived from poxviruses, Herpes simplex virus I, adenoviruses and adeno-associated viruses. However, any method of introducing the vector into a cell that mediates the integration of that vector into the host cell genome, or that permits the vector to be stably maintained in the host cell in the absence of genomic DNA integration, e.g., autonomous replication, is within the scope of the invention. Most of the current and proposed gene therapy clinical protocols employ retroviral vectors.

Furthermore, a vector useful in the practice of the invention can comprise promoter and/or transcriptional enhancer sequences operably linked to the preselected DNA segment. For example, the γ-actin promoter, the phosphoglycerate kinase promoter and many of the retroviral and retrotransposon long terminal repeats can promote transcription of linked sequences in HSC. Other promoters and/or transcriptinal enhancer elements useful in the practice of the invention are known to those of skill in the art.

Retroviruses are single-stranded RNA viruses which replicate viral RNA into DNA by reverse transcription. Upon replication in the host cell, the viral DNA is inserted into the host chromosome, where it becomes a provirus. Due to their efficiency at integrating into host cells, retroviruses are considered to be among the most promising vectors for human gene therapy. These vectors have a number of properties that lead them to be considered promising for genetic therapy of disease. These include: (1) efficient entry of genetic material present in the vector into cells; (2) an efficient process of entry into target cell nucleus; (3) relatively high levels of gene expression; (4) minimal pathological effects on target cells; and (5) the potential to target to particular cellular subtypes through control of the vector-target cell binding and tissue specific control of gene expression.

Retroviral genomes consist of cis-acting and trans-acting gene sequences. The cis regions include the long terminal repeat (LTR) transcriptional promoter and DNA integration sites, the two primer binding sites required for reverse transcription of DNA from viral RNA, and the packaging signals required for efficient packaging of viral RNA into virions. The LTR is found at both ends of the proviral genome. Trans-functions include the proteins encoded by the gag, pol, and env genes, which are located between the LTRs. Gag and pol encode, respectively, internal viral structural and enzymatic proteins. Env encodes the viral glycoprotein which confers infectivity and host range specificity on the virus. A retroviral vector generally consists of cis sequences and the replacement of the trans sequences with a gene(s) of interest. The trans functions can be provided by expression the trans sequences in a helper cell or by a helper virus. See U.S. Pat. No. 5,354,674 for a discussion of the use of retrotransposon vectors, which are related to retroviral vectors, in mammalian gene transfer. For a more detailed description of the retroviral life cycle, retroviral cis and trans sequences, as well as retroviral vectors, see *RNA Tumor Viruses: Molecular Biology of Tumor Viruses,* Weiss et al. (eds), 2nd ed., Cold Spring Harbor, vols. 1 and 2 (1984).

While previous results indicated that retroviral infection of HSCs is relatively inefficient, most likely due to the quiescent state of a vast majority of HSCs, recent evidence suggests that up to 50% of human steady state bone marrow derived long term culture initiating cells (LTC-IC) can be transduced with a retroviral vector when those cells are pre-incubated with stromal conditioned media (SCM$^+$) containing IL3 (IL3$_x$) and MIP-1α, and when LTC-IC are cocultured with stromal feeders, FN, or immobilized β1-integrin antibodies during the transduction period. LTC-IC are cells that can initiate and sustain long term bone marrow cultures in vitro, and can differentiate into myeloid, B-lymphoid, natural killer cell, and T-cell lineages when induced to differentiate in vitro by chemical or physical methods, or in vivo by transplant into xenogeneic recipients. Thus, culture conditions can be modified to enhance the transduction of HSCs by retroviral vectors.

The invention will be further described by reference to the following detailed examples.

EXAMPLE I

Characterization of Mutant DHFR Transgenic Mice

Because hematopoietic stem cells are a relatively quiescent cell population, in general these cells are quite resistant to MTX. The rationale for the administration of MTX immediately post-transplant is based on the idea that stem cells must replicate to some extent during the process of engrafinent, making them susceptible to MTX selection at that time. The availability of DHFR transgenic mice could provide a unique resource for quantitative studies of selective engraftment, since these mice can be used as a source of donor marrow in which 100% of the cells contain the drug-resistance gene.

To provide a source of DHFR containing HSC, a series of inbred FVB/N mice were used to make FVB/N transgenic mice which express the arg22, trp31 or tyr22 murine DHFR variants, which confer resistance to MTX. MTX resistant variants of mammalian DHFRs have been generated by cloning DHFR genes from MTX resistance cell lines, and by site directed mutagenesis. MTX resistant variants of dihydrofolate reductase (DHFR) useful in the practice of the invention include, but are not limited to, SER$^{31}$-DHFR, ASN$^{31}$-DHFR, HIS$^{31}$-DHFR, SER$^{34}$-DHFR, TYR$^{22}$-DHFR, TRP$^{31}$-DHF, ARG$^{22}$-DHFR, TRP$^{22}$-DHFR, and PHE$^{22}$-DHFR (see Morris and McIvor, *Biochem. Pharmacol.,* 47, 1207 (1994)).

Line 03 (trp31) and line 04 (arg22) DHFR transgenic mice were found to be more tolerant to MTX than normal animals after sublethal irradiation and daily drug administration at levels of MTX which were 25% the daily dose shown to be lethal for normal FVB/N mice (0.25 mg/kg/day for 1–4 days, 0.5 mg/kg/day for the next four days, then 1.0 mg/kg/day for the remaining time).

Transplantation of 10$^6$ bone marrow cells from line 04 DHFR transgenic mice into normal, irradiated mice rendered the recipient animals resistant to MTX at levels of methotrexate which caused hematopoietic toxicity in bone marrow recipients that received non-transgenic marrow (0.25 mg/kg/day for 1–4 days, 0.5 mg/kg/day for the next four days, then 1.0 mg/kg/day for the remaining time). Although marrow from line 03 was found to protect transplant recipients from lethal, low-dose MTX toxicity, line 03 marrow was not as effective as line 04 marrow in protecting recipient animals.

Transplantation of 10$^7$ cells from either line 03 or line 04 DHFR transgenic marrow conferred upon normal irradiated recipient animals resistance to a high dose of MTX (final of 4 mg/kg/day), a level which causes not only hematopoietic toxicity but gastrointestinal toxicity as well. Surprisingly, gastrointestinal cells in animals transplanted with DHFR transgenic marrow were significantly less affected than control animals by the high dose of MTX, indicating that the protective effect of the transgene was systemic, i.e., proliferating tissue which did not contain the transgene was nevertheless protected by the presence of the transgenic HSC. Therefore, drug resistant DHFR expression in hematopoietic cells can provide significant protection from MTX toxicity in animals.

These results suggest a key role for hematopoietic cells in mediating the sensitivity or resistance of animals to MTX. Thus, chemoprotection by MTX-resistant DHFR gene transfer might not be limited to special circumstances that render hematopoietic tissues particularly sensitive to MTX such as extreme cytoreduction and bone marrow transplantation. The present method may be used to permit irradication of MTX-sensitive tumors not usually treated by total body irradiation plus bone marrow transplantation, and for which MTX toxicity to normal tissues limits the utility of MTX.

EXAMPLE II

Competitive Repopulation of Recipients with Normal and DHFR Transgenic Marrow

A. Competitive Repopulation with 50/50 Mixtures of Normal and Transgenic Marrow at High Dose (4 mg/kg/day) MTX Mice which were transplanted with 10$^7$ DHFR transgenic marrow cells were protected from the lethal MTX toxicity observed in animals transplanted with 10$^7$ normal FVB/N donor marrow cells (Example I). Although the ability of a donor marrow population to confer drug-resistance does not necessarily imply that this population is capable of selective engrafiment under similar conditions, in vivo methotrexate selection may be effective to engraft MTX-resistant transgenic stem cells since there may be sufficient proliferative activity during engraftment to prevent nontransgenic stem cells from engrafting.

To determine if DHFR expression in donor marrow allows selective engraftment in transplant recipients, normal female FVB/N animals were administered a lethal dose of Cs irradiation (900 rads) and then transplanted with approximately 10$^7$ donor marrow cells consisting of (i) 100% normal male FVB/N marrow, (ii) 100% female line 04 DHFR transgenic marrow (or marrow from another mutant DHFR transgenic line), or (iii) a 50/50 mixture of normal male FVB/N marrow and female DHFR transgenic marrow. Male marrow is used as competitor so that Y chromosome sequences can be used as a quantitative signal for the presence of competitor-derived material at the time of analysis, while the DHFR transgene can be used as a quantitative signal for presence of DHFR-transgenic-derived material.

Animals in each of the three groups were administered either PBS or MTX at an increasing dose schedule culminating at 4 mg/kg/day. MTX administration was continued out to 60 days post-transplant. Under these conditions of MTX administration, all animals transplanted with FVB/N marrow and administered MTX succumb to MTX induced toxicity at 15–30 days post-transplant. After 60 days, MTX administration is stopped. A small number of animals were sacrificed at this time to collect marrow samples for subsequent analysis, but most of the animals were maintained for an additional 2 months. At 4 months post-transplant, all surviving animals were sacrificed and bone marrow harvested. Each marrow sample collected was resuspended and then injected into 5 lethally-irradiated secondary female FVB/N recipients ($2 \times 10^6$ donor cells per secondary recipient), saving the leftover marrow for subsequent molecular analysis. Secondary recipients were maintained for an additional 4 months before sacrificing and harvesting marrow samples.

To ensure that all of the marrow cells in the tested sample are derived from primitive, hematopoietic stem cells contained in the original inoculum, experiments are conducted for a full eight months and include transplantation to a secondary recipient. These precautions are necessary because the life span of more differentiated transgenic marrow cells in the original inoculum is from several days up to 2–3 months.

DNA was extracted from bone marrow samples, digested with BgII, electrophoresed on agarose gels and then blotted onto Nytran. Each blot was first probed for DHFR sequences as previously described by May et al. (*Blood*, 86, 2439 (1995)), and then the blot is stripped and reprobed for Y chromosome sequences using the plasmid pY2 (kindly provided by Dr. Ihor Lemischka, Princeton University).

After hybridization with each probe, the radioactivity associated with DHFR or Y sequences was quantitated using a Molecular Dynamics Phosphorimager. Controls of normal FVB/N male DNA, normal FVB/N female DNA, and DHFR transgenic female DNA were included on each blot to allow quantitation of relative cellular representation, using the signal from the endogenous DHFR gene as a loading control. The contribution of DHFR transgenic marrow was quantitated as the ratio of the DHFR transgene signal strength to endogenous DHFR gene signal, relative to the same ratio for the 100% control (i.e., the DHFR transgenic female sample). The contribution of competitor marrow was quantitated as the ratio of Y sequence signal strength to endogenous DHFR gene signal, relative to the same ratio for the normal FVB/N male control. The two signals do not always add up to 100%, since radiation-resistant host-derived material can contribute to the ultimate marrow cellularity, and in this case would contribute to the endogenous DHFR gene signal but not to either the Y signal or the DHFR transgene signal. Quantitation of several samples (1 primary and 6 secondary) from each marrow transplant allows assessment of the statistical significance of the results.

Figure 1:
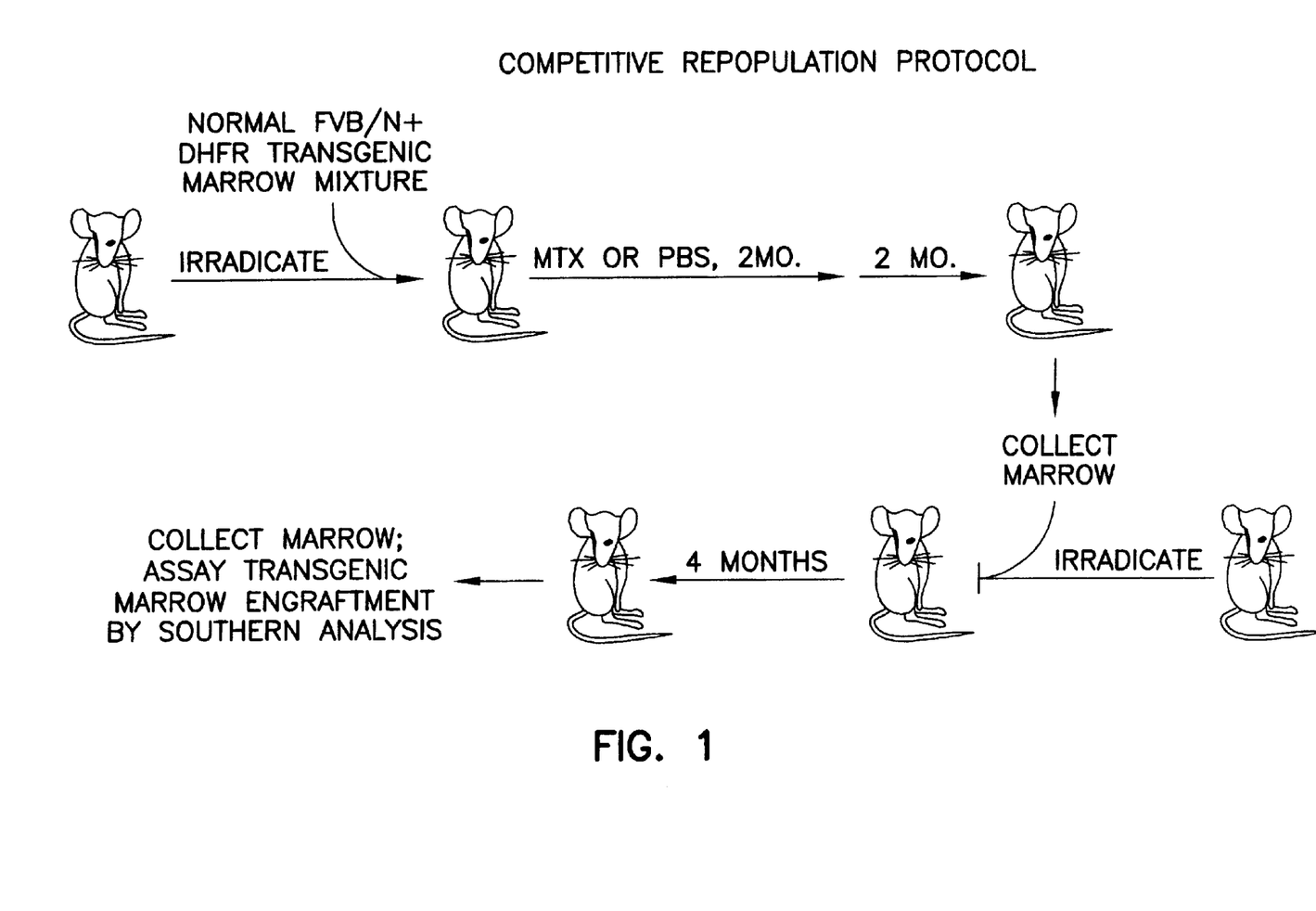
FIG. 1 depicts a competitive repopulation protocol to selectively engraft DHFR transgenic marrow into an irradiated recipient. MTX=methotrexate. DHFR=dihydrofolate reductase.
Figure 2:
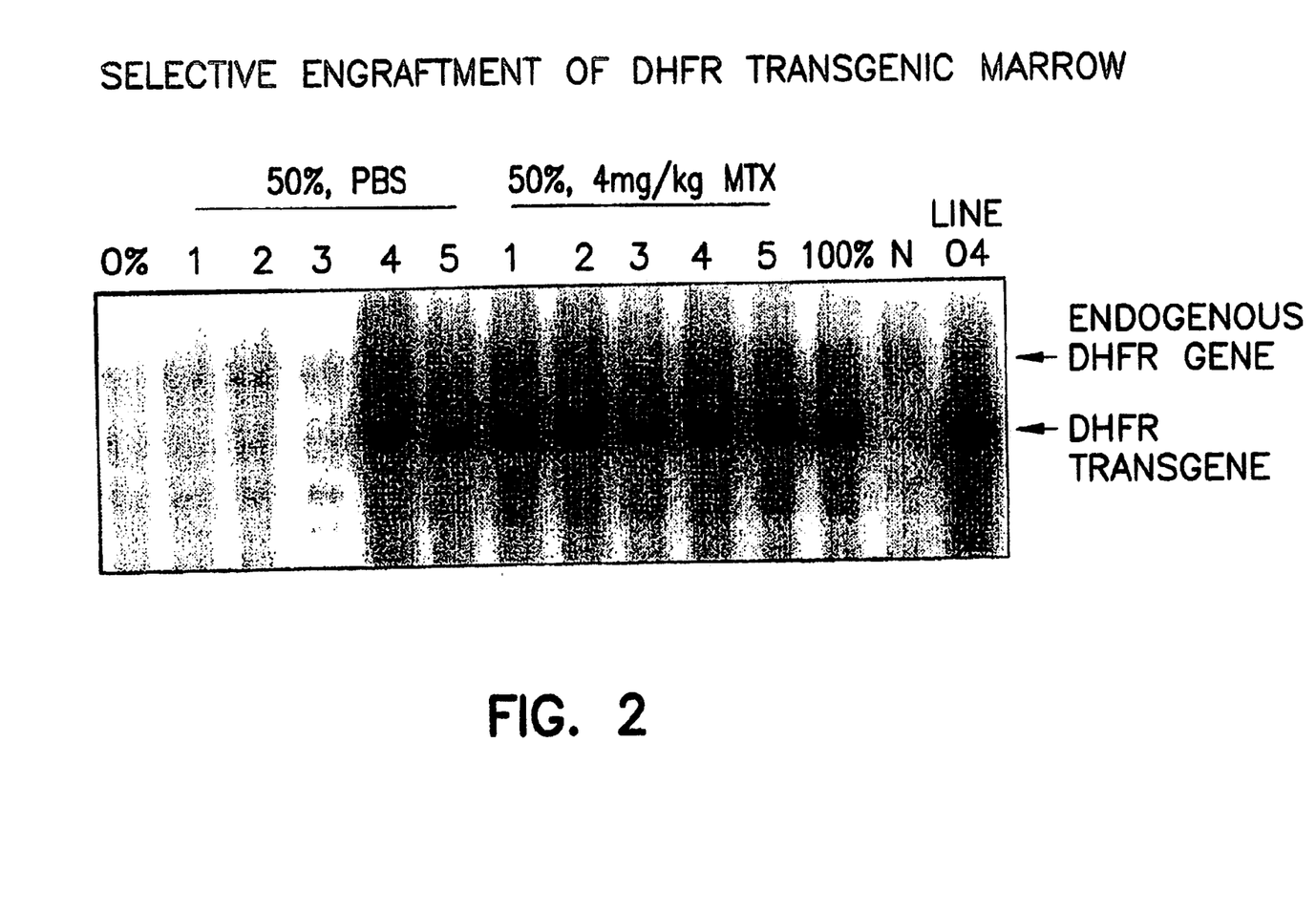
FIG. 2 depicts a Southern blot of DNAs isolated from the bone marrow of mice that underwent the competitive protocol shown in FIG. 1. DNAs were restricted with BglII. Lane I contains marrow DNA from a control female mouse that was transplanted with normal, nontransgenic marrow. Lanes 2–6 contain marrow DNA from five mice that were secondary recipients of marrow from PBS-administered animals that received a primary transplant comprising 50% normal marrow and 50% DHFR transgenic marrow. Lanes 7–11 contain marrow DNA from secondary recipients of marrow from MTX-administered animals that received a primary transplant comprising 50% normal marrow and 50% DHFR transgenic marrow. Lane 12 contains marrow DNA from a mouse that was a secondary recipient of marrow from an animal that received a primary transplant comprising 100% DHFR transgenic marrow. Lane 13 contains marrow DNA from a control male mouse that did not undergo the protocol. Lane 14 contains marrow DNA from a DHFR transgenic mouse. The position of the endogenous DHFR gene and the introduced transgene is shown at the right.

Only 2 out of 5 secondary recipients of PBS-administered animals showed a significant contribution of transgenic marrow, while all 5 out of 5 secondary recipients of MTX-administered animals showed a substantial contribution of transgenic marrow, i.e., approximately that observed from injection of 100% transgenic marrow in the primary recipients (FIG. 2). The presence and expression of the drug-resistance gene in the transgenic marrow provided the transplanted transgenic marrow with a selective advantage over the normal marrow in establishing a bone marrow graft in the primary recipients. Moreover, animals transplanted with transgenic marrow exhibit a substantial increase in DHFR transgene copy number in primary recipients that had been administered MTX rather than PBS. Therefore, MTX can be used for selective engraftment of stem cells expressing a MTX-resistant DHFR, which leads to an increase in the relative number of MTX-resistant cells in hematopoietic tissues.

B. Competitive Repopulation at Low Dose (1 mg/kg/day) MTX.

Transplantation of $10^6$ DHFR transgenic marrow cells protected recipient mice from MTX toxicity at levels up to 1 mg/kg/day (Example 1). Thus, by decreasing the size of the graft, the level of MTX which is tolerated by the recipient animal can be decreased. To determine if MTX administration at a lower dose along with transplantation at a lower cell dose more effectively provides for selective engraftment of DHFR transgenic stem cells, female FVB/N animals are given a lethal dose of total body irradiation (900 rads cesium) and then transplanted with a total of $10^6$ donor marrow cells consisting of the same groups described above, i.e., (i) 100% normal male FVB/N marrow, (ii) 100% female line 04 DHFR transgenic marrow (or marrow from another mutant DHFR transgenic line), or (iii) a 50/50 mixture of normal male FVB/N marrow and female DHFR transgenic marrow.

These animals are administered either PBS or MTX at an increasing dose schedule culminating at 1 mg/kg/day for 60 days. The animals will be maintained until 4 months post-transplant, sacrificed for marrow harvest, and the marrow used for secondary transplants at a dose of $2 \times 10^6$ donor cells. Secondary transplant recipients are maintained for 4 months and then sacrificed to collect marrow cells for quantitative Southern hybridization analysis as described above.

A significant increase in the contribution of DHFR transgene sequences associated with MTX administration in animals transplanted with a 50/50 mixture of normal male FVB/N and DHFR transgenic marrow is evidence for selective engraftment of DHFR transgenic stem cells under the conditions used for this experiment (i.e., $10^6$ cells transplanted, MTX administered at 1 mg/kg/day).

C. Competitive Repopulation of Reduced Proportions of DHFR Transgenic Marrow Cells.

The competitive repopulation experiments described above test for MTX-mediated selective engraftment of DHFR transgenic marrow cells after transplantation of a 50/50 mixture of normal and transgenic marrow. However, transplantation with a smaller proportion of DHFR transgenic marrow cells may be necessary in order to assess a significant MTX-mediated increase in the contribution of these cells to hematopoiesis in primary or secondary recipients. To determine whether a smaller contribution of transgenic marrow cells can contribute to engraftment in secondary recipients, animals are irradiated and then transplanted with $10^6$ or $10^7$ donor marrow cells consisting of the following ratios of DHFR transgenic marrow to normal male FVB/N marrow; 50/50, 20/80, and 5/95. Animals transplanted with $10^6$ donor marrow cells are administered PBS, or MTX at a final dose of 1 mg/kg/day, and animals transplanted with $10^7$ cells are administered a final dose of 4 mg/kg/day. MTX is administered for 60 days, then animals are maintained without injections for another two months before sacrifice and transplantation into secondary lethally-irradiated recipients (5 secondary recipients per primary recipient, $2 \times 10^6$ donor cells per animal). Secondary recipients are maintained for 4 months before sacrifice and collection of marrow for determination of relative donor marrow contribution by Southern hybridization analysis as described above.

Any significant increase in the relative contribution of DHFR transgenic marrow observed for MTX administered animals versus PBS administered animals is evidence for selective engraftment of DHFR transgenic marrow under the conditions tested (with respect to the number of cells transplanted, the dose of MTX administered, and the ratio of DHFR transgenic marrow cells to normal male FVB/N competitor cells).

D. Conclusions

Thus, the method of the present invention can enrich for transgenic stem cells and selectively engraft those stem cells after transplantation even when the transgenic cells comprise a low proportion of the transplanted donor cell population. This approach is clinically useful as a way to improve the representation of transgenic hematopoietic cells post-transplant in spite of an initially low transformation frequency. The result is that the successfully transformed stem cells can rapidly contribute a much greater fraction of the marrow cells in the recipient patient than they do to the original fraction of transformed marrow cells, thus effectively counteracting the low frequency of gene transfer. The invention described herein is thus applicable to any gene therapy protocol which targets hematopoietic stem cells, through the preparation of gene delivery vehicles which contain not only a preselected DNA segment encoding a therapeutic molecule, but also contain a preselected DNA segment encoding resistance to an agent. Such a protocol can include the daily administration of the agent, wherein the administration begins soon, or immediately, after the transformed cells are transplanted into a recipient.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method in which transgenic hematopoietic stem cells having a selective advantage over nontransgenic hematopoietic cells for engraftment are maintained in the mammal in the absence of selection, comprising:
   (a) administering a series of doses of a composition comprising an anti-folate, a vinca alkaloid, or an anthracycline to a mammal transplanted with a population of hematopoietic cells, at least a portion of which comprises a transgenic hematopoietic stem cell and a nontransgenic hematopoietic stem cell, wherein the genome of the transgenic hematopoietic cell has been augmented in vitro by a recombinant DNA comprising a promoter functional in hematopoietic stem cells operably linked to a first preselected DNA segment which encodes resistance or tolerance to the anti-folate, vinca alkaloid, or anthracycline, wherein the expression of the recombinant DNA in the transgenic hematopoietic stem cell in the mammal and the administration of the series of doses to the mammal results in a mammal in which the transgenic hematopoietic stem cell has a selective advantage in bone marrow engraftment relative to the nontransgenic hematopoietic cell; and
   (b) identifying a mammal from (a) in which a transgenic hematopoietic stem cell has engrafted and which mammal comprises progeny of the transgenic hematopoietic stem cell which are maintained in the mammal in the absence of the administration of the anti-folate, vinca alkaloid, or anthracycline.

2. The method of claim 1 further comprising augmenting the genome of the transgenic stem cell with a second preselected DNA segment, which encodes a therapeutic agent, and which is linked to the first preselected DNA segment.

3. The method of claim 1 wherein the first preselected DNA segment encodes a methotrexate resistant dihydrofolate reductase.

4. The method of claim 3 wherein the dihydrofolate reductase is SER$^{31}$-DHFR.

5. The method of claim 3 wherein the dihydrofolate reductase is SER$^{34}$-DHFR.

6. The method of claim 3 wherein the dihydrofolate reductase is TYR$^{22}$-DHFR.

7. The method of claim 3 wherein the dihydrofolate reductase is TRP$^{31}$-DHFR.

8. The method of claim 3 wherein the dihydrofolate reductase is ARG$^{22}$-DHFR.

9. The method of claim 3 wherein the dihydrofolate reductase is PHE$^{22}$-DHPR.

10. The method of claim 3 wherein the dihydrofolate reductase is HES$^{31}$-DHFR.

11. The method of claim 3 wherein the dihydrofolate reductase is TRP$^{22}$-DHFR.

12. The method of claim 3 wherein the dihydrofolate reductase is ASN$^{31}$-DHFR.

13. The method of claim 1 wherein the first preselected DNA segment is the mdr1 gene.

14. The method of claim 1 wherein the administration begins within 48 hours of stem cell transplantation.

15. The method of claim 1 wherein the mammal is a human.

16. The method of claim 1 wherein the mammal is subjected to chemotherapy or radiation therapy prior or subsequent to the transplantation of the stem cells.

17. The method of claim 1 wherein methotrexate is administered.

18. A method for conferring a selective advantage for engraftment to a transgenic hematopoietic stem cell relative to a nontrasgenic hematopoietic cell in a mammal transplanted with transgenic hematopoietic and nontangenic hematopoietic cells, comprising: administeg a series of doses of a composition comprising an anti-folate, a vinca alkaloid, or an anthracycline to a mammal transplanted with a population of hematopoietic cells, at least a portion of which comprises a transgenic hematopoietic stem cell and a nontransgenic hematopoietic stem cell, wherein the genome of the transgenic hematopoietic cell has been augmented in vitro by a recombinant DNA comprising a promoter functional in hematopoietic stem cells operably linked to a first preselected DNA segment which encodes resistance or tolerance to the anti-folate, vinca alkaloid, or anthracycline, and wherein the expression of the recombinant DNA in the transgenic hematopoietic stem cell in the mammal and the administration of the series of doses to the mammal results in a mammal in which the transgenic hematopoietic stem cell has a selective advantage in bone marrow engrafment relative to the nontransgenic hematopietic cell.

19. The method of claim 18 further comprising augmenting the genome of the transgenic stem cell with a second preselected DNA segment, which encodes a therapeutic agent, and which is linked to the fist preselected DNA segnent.

20. The method of claim 18 wherein the first preselected DNA segment encodes a metotrexate resistant dihydrofolate reductase.

21. The method of claim 20 wherein the dihydrofolate reductase is SER$^{31}$-DHFR.

22. The method of claim 20 wherein the dihydrofolate reductase is SER$^{34}$-DHFR.

23. The method of claim 20 wherein the dihydrofolate reductase is TYR$^{22}$-DHFR.

24. The method of claim 20 wherein the dihydrofolate reductase is TYR$^{31}$-DHFR.

25. The method of claim 20 wherein the dihydrofolate reductase is ARG$^{22}$-DHFR.

26. The method of claim 20 wherein the dihydrofolate reductase is PHE$^{22}$-DHFR.

27. The method of claim 20 wherein the dihydrofolate reductase is HIS$^{31}$-DHFR.

28. The method of claim 20 wherein the dihydrofolate reductase is TRP$^{22}$-DHFR.

29. The method of claim 20 wherein the dihydrofolate reductase is ASN$^{31}$-DHFR.

30. The method of claim 18 wherein the first preselected DNA segnent is the mdr1 gene.

31. The method of claim 18 wherein the administration begins within 48 hours of stem cell transplantation.

32. The method of claim 18 wherein the mammal is a human.

33. The method of claim 18 wherein the mammal is subjected to chemotherapy or radiation therapy prior or subsequent to the transplantation of the stem cells.

34. The method of claim 18 wherein methotrexate is administered.

* * * * *

UNITED STATES PATENT AND TRADEMARK OFFICE
CERTIFICATE OF CORRECTION

PATENT NO.   : 6,485,722 B1
DATED        : November 26, 2002
INVENTOR(S)  : R. S. McIvor, Rohaizah I. James and Chad May

It is certified that error appears in the above-identified patent and that said Letters Patent is hereby corrected as shown below:

Column 11,
Line 38, insert -- for preparing a mammal engrafted with transgenic hematopoietic stem cells -- after "A method".

Column 12,
Line 59, delete "fist" and insert -- first -- therefor.
Line 60, delete "segnent" and insert -- segment -- therefor.
Line 62, delete "metotrexate" and insert -- methotrexate -- therefor.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,485,722 B1  Page 1 of 1
DATED : November 26, 2002
INVENTOR(S) : McIvor et al.

It is certified that error appears in the above-identified patent and that said Letters Patent is hereby corrected as shown below:

Column 1,
Line 4, insert --
                Statement of Government Rights
The invention was made, at least in part, with a grant from the Government of the United States of America (National Institutes of Health #R01-CA60803). The Government may have certain rights to the invention. --.

Signed and Sealed this

Fourth Day of November, 2003

JAMES E. ROGAN
*Director of the United States Patent and Trademark Office*